(12) United States Patent
Park

(10) Patent No.: US 8,211,006 B2
(45) Date of Patent: Jul. 3, 2012

(54) HEALTH APPARATUS FOR MAN

(76) Inventor: Myung Chan Park, Jinju-si (KR)

( * ) Notice: Subject to any disclaimer, the term of this patent is extended or adjusted under 35 U.S.C. 154(b) by 417 days.

(21) Appl. No.: 12/602,695

(22) PCT Filed: Jun. 3, 2008

(86) PCT No.: PCT/KR2008/003099
§ 371 (c)(1),
(2), (4) Date: Dec. 2, 2009

(87) PCT Pub. No.: WO2008/150087
PCT Pub. Date: Dec. 11, 2008

(65) Prior Publication Data
US 2010/0179379 A1    Jul. 15, 2010

(30) Foreign Application Priority Data
Jun. 5, 2007    (KR) .......................... 10-2007-0054808

(51) Int. Cl.
*A61F 5/00*    (2006.01)
(52) U.S. Cl. ........................................................ 600/39

(58) Field of Classification Search .............. 600/38–41; 128/897, 898
See application file for complete search history.

(56) References Cited

U.S. PATENT DOCUMENTS

| | | | | |
|---|---|---|---|---|
| 3,759,254 A * | 9/1973 | Clark | ............................... | 600/39 |
| 4,224,933 A * | 9/1980 | Reiling | ........................... | 600/39 |
| 4,240,413 A * | 12/1980 | Hanus | ............................... | 600/41 |
| 5,306,227 A | 4/1994 | Osbon | | |

* cited by examiner

*Primary Examiner* — Samuel Gilbert
(74) *Attorney, Agent, or Firm* — John K. Park; Park Law Firm

(57) ABSTRACT

A penis erection stabilizer wherein a through-hole is defined through a center portion of a stabilizer body having a cylindrical configuration so that the penis can be inserted through the through-hole, and a small diameter portion having a diameter less than that of the through-hole is formed at a front end of the through-hole. According to the present invention, advantages are conferred in that the penis erection stabilizer has a single body and a small diameter portion is formed at the front end of a through-hole so that the blood can be easily supplied to the penis and the discharge of the blood from the penis can be maximally retarded, thereby maintaining the erected state of the penis for a time sufficient for the completion of the sexual act.

7 Claims, 6 Drawing Sheets

[Fig. 1]
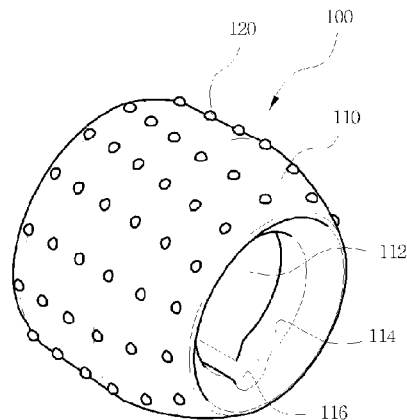
[Fig. 2]
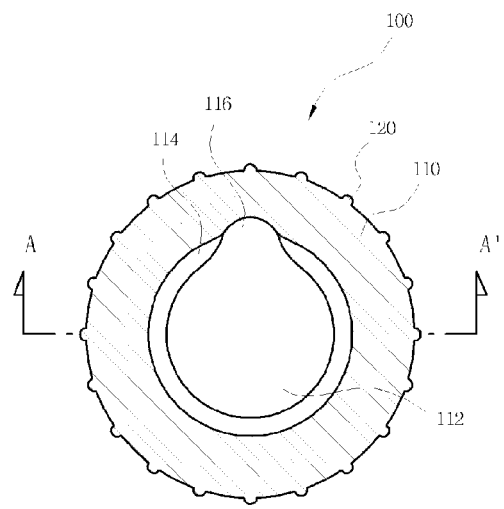
[Fig. 3]
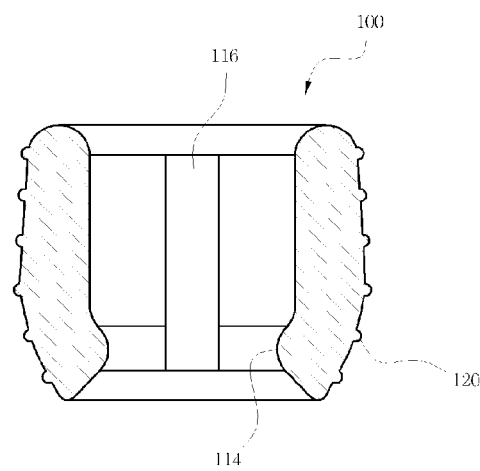

[Fig. 4]
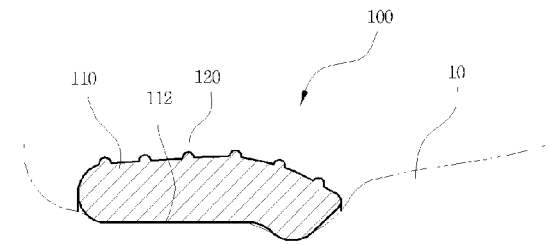
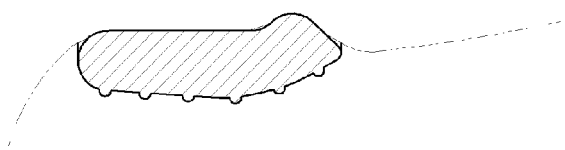
[Fig. 5]
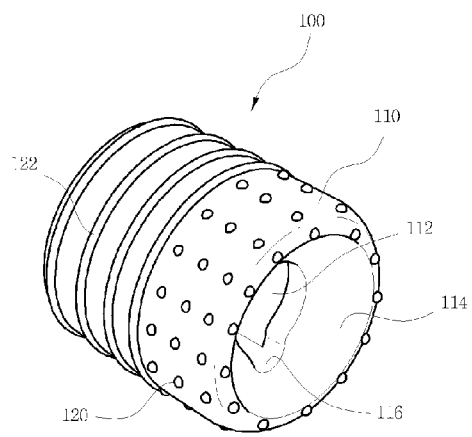
[Fig. 6]
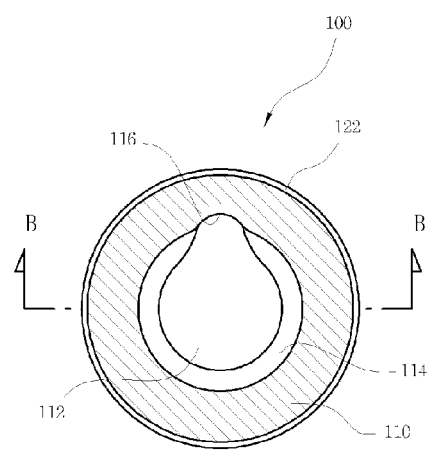

[Fig. 7]
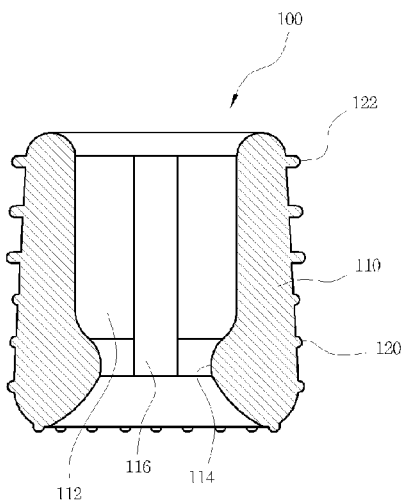
[Fig. 8]
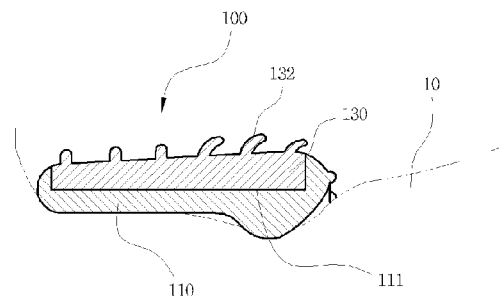
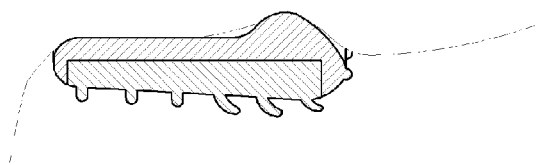
[Fig. 9]
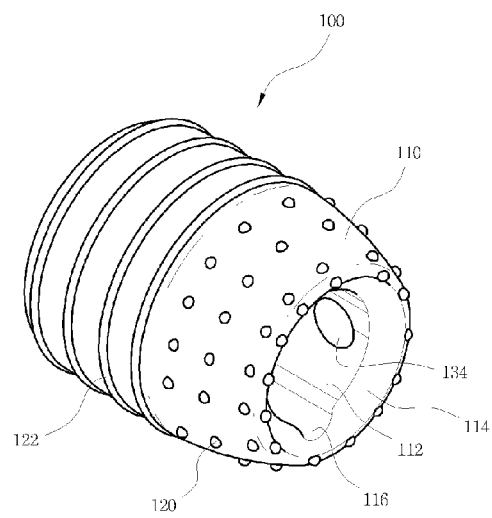

[Fig. 10]
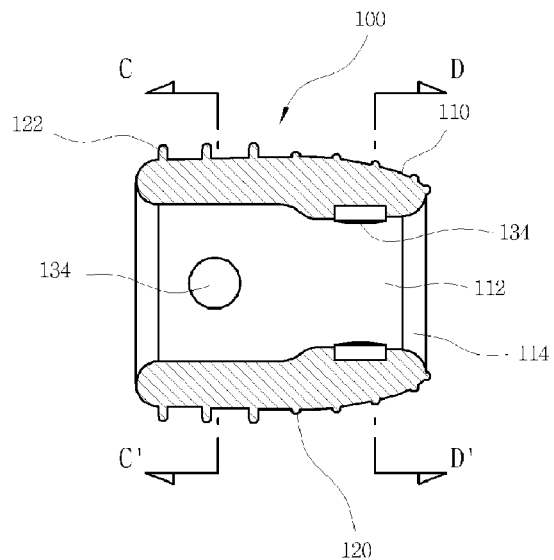
[Fig. 11]
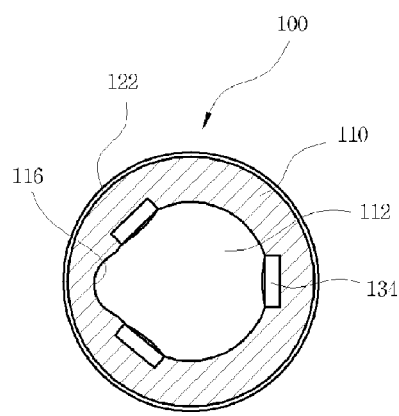
[Fig. 12]
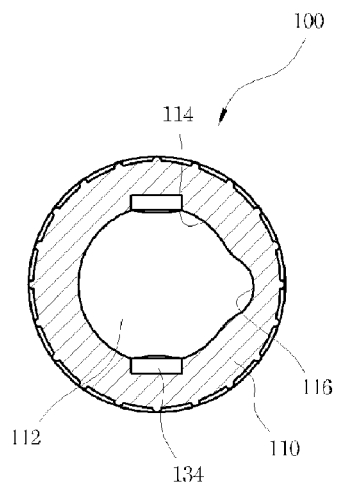

[Fig. 13]
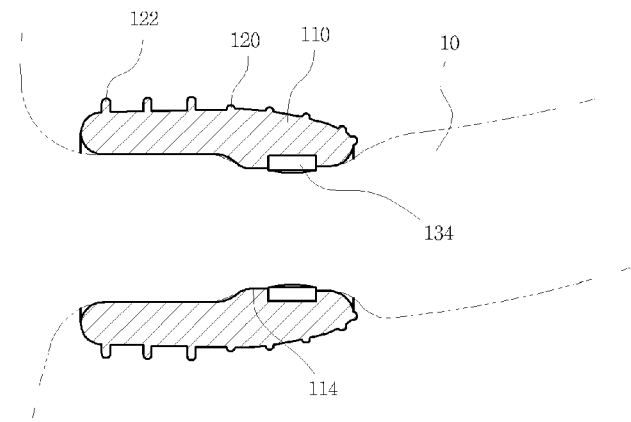
[Fig. 14]
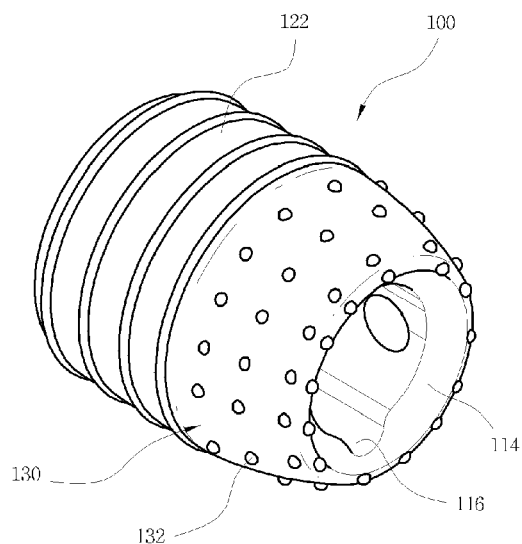
[Fig. 15]
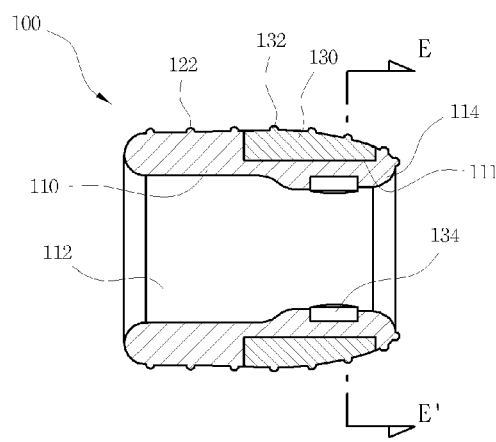

[Fig. 16]
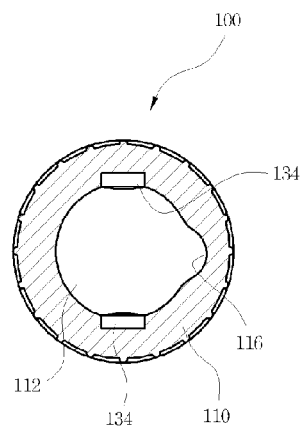
[Fig. 17]
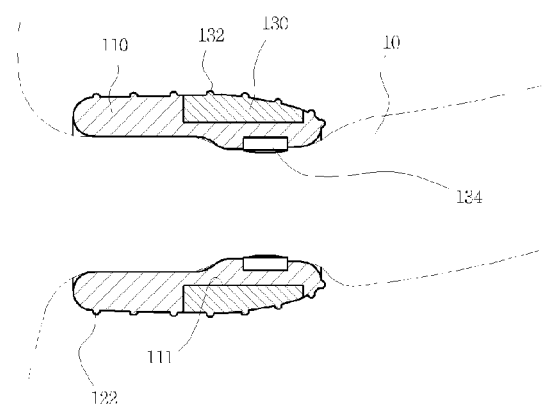
[Fig. 18]
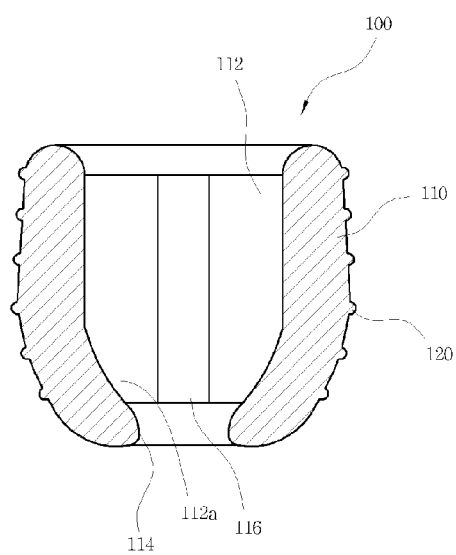

HEALTH APPARATUS FOR MAN

TECHNICAL FIELD

The present invention relates to a health apparatus for a man, and more particularly, to a penis erection stabilizer which has an integral structure to be mounted on the base of a male penis and to maintain the erected state of the penis for a time sufficient for the completion of the sexual act when the penis is erected by the blood supply into the penis.

BACKGROUND ART

In general, the erection of the penis is caused due to combined functions of the nerves, the blood vessels and the endocrine system such as pituitary hormone, and the male penis has a peculiar structure to react on these combined functions. The male penis has spongy tissue like a sponge that includes a number of blood vessels. If a sexual stimulus is applied in a visual or tactile course, as the blood vessels in the penis are expanded, a large amount of blood is supplied into the penis, and the penis is expanded and erected by blood pressure. These days, as males are exposed to complicated social circumstances and stresses due to heavy work, they suffer impotence and premature ejaculation, so that they cannot lead harmonious sexual act with their wives.

Under these circumstances, various measures for ensuring harmonious sexual act have been disclosed in the art. A typical example is a penis erection stabilizer having the shape of an O-ring.

However, this stabilizer ring has a problem in that it has a fixed diameter. When the stabilizer ring is put on the penis, after the blood is supplied into the spongy tissue of the penis through an artery and the penis is expanded, the stabilizer ring retards the blood from being discharged through a vein, so that the erected state of the penis can be maintained. However, another problem is caused in that, because the pressure of the stabilizer ring is dull, the duration of the erected state of the penis becomes short.

Meanwhile, another penis erection stabilizer has been disclosed in U.S. Pat. No. 6,319,194. This penis erection stabilizer has a structure in which an outer ring and an inner ring are connected with each other by a sheath. In order to put on the penis erection stabilizer, the outer ring, to which the inner ring is connected through the sheath, is first mounted on the penis, and then, the inner ring is rotated on the penis while rolling the sheath, to be placed next to the base of the penis. Finally, the inner ring is placed inside the outer ring so that the outer ring is disposed around the inner condom, since the outer ring is first mounted on the penis and then the inner ring is rotated while rolling the sheath, inconvenience is caused in the use of the penis erection stabilizer. Also, since hair is likely to be captured in the sheath, a wound may be caused, and depending upon a situation, as the inner ring and the outer ring overlap with each other, the penis is likely to be severely compressed so that the blood circulation is blocked.

In order to cope with these problems, the present applicant has disclosed still another penis erection stabilizer in Korean Utility Model Registration No. 0422632. The penis erection stabilizer is composed of a cylindrical body which has a first through-hole defined through the center portion thereof and having a predetermined diameter and is primarily put on the penis to be placed adjacent to the base of the penis, and an O-ring which has a second through-hole defined through the center portion thereof and having a diameter less than that of the first through-hole and is secondarily put on the penis with the cylindrical body put on the penis. In this penis erection stabilizer, when the blood sequentially passes through the cylindrical body and the O-ring, since the diameter of a path gradually decreases, the blood is supplied into and expands the penis so that the erection degree of the penis can be elevated. When the blood is discharged from the penis through a vein, while the blood in the penis must pass through the O-ring, because the O-ring has the diameter abruptly decreasing when compared to the penis, the discharge of the blood is retarded so that the duration of the erected state of the penis can be extended.

Nonetheless, because this penis erection stabilizer is divisionally composed of the cylindrical body and the O-ring, if any one of them is broken or lost, the penis erection stabilizer cannot be properly used. Further, since the penis erection stabilizer has a slippery surface, inconvenience is caused when putting it on and off.

Moreover, due to the fact that the penis erection stabilizer is divisionally composed of the cylindrical body and the O-ring, the manufacturing cost increases.

DISCLOSURE OF INVENTION

Technical Problem

Accordingly, the present invention has been made in an effort to solve the problems occurring in the related art, and an object of the present invention is to provide a penis erection stabilizer which comprises a single cylindrical body for sufficiently delaying a time the blood supplied through an artery into the penis is discharged through a vein so that the erected state of the penis can be maintained for a time sufficient for the completion of the sexual act, and which has a structure to be easily mounted on and removed from the penis.

Technical Solution

In order to achieve the above object, according to one aspect of the present invention, there is provided a penis erection stabilizer wherein a through-hole is defined through a center portion of a stabilizer body having a cylindrical configuration so that the penis can be inserted through the through-hole, and a small diameter portion having a diameter less than that of the through-hole is formed at a front end of the through-hole.

ADVANTAGEOUS EFFECTS

Thanks to the above features, according to the present invention, advantages are conferred in that the penis erection stabilizer has a single body and a small diameter portion 114 is formed at the front end of a through-hole 112 so that the blood can be easily supplied to the penis and the discharge of the blood from the penis can be maximally retarded, thereby maintaining the erected state of the penis for a time sufficient for the completion of the sexual act.

Further, due to the fact that the penis erection stabilizer 100 is formed to have the single body 110, the manufacture of the penis erection stabilizer can be simplified, and the manufacturing costs can be decreased. Also, when compared to the conventional penis erection stabilizer composed of several parts, the probability of being lost decreases.

BRIEF DESCRIPTION OF THE DRAWINGS

FIG. 1 is a perspective view illustrating a penis erection stabilizer in accordance with a first embodiment of the present invention.

FIG. 2 is a sectional view illustrating the penis erection stabilizer shown in FIG. 1.

FIG. 3 is a sectional view taken along the line A-A' of FIG. 2.

FIG. 4 is a sectional view illustrating the use of the penis erection stabilizer shown in FIG. 1.

FIG. 5 is a perspective view illustrating a penis erection stabilizer in accordance with a second embodiment of the present invention.

FIG. 6 is a sectional view illustrating the penis erection stabilizer shown in FIG. 5.

FIG. 7 is a sectional view taken along the line B-B' of FIG. 6.

FIG. 8 is a sectional view illustrating a penis erection stabilizer in accordance with a third embodiment of the present invention.

FIG. 9 is a perspective view illustrating a penis erection stabilizer in accordance with a fourth embodiment of the present invention.

FIG. 10 is a sectional view illustrating the penis erection stabilizer shown in FIG. 9.

FIG. 11 is a sectional view taken along the line C-C' of FIG. 10.

FIG. 12 is a sectional view taken along the line D-D' of FIG. 10.

FIG. 13 is a sectional view illustrating the use of the penis erection stabilizer shown in FIG. 9.

FIG. 14 is a perspective view illustrating a penis erection stabilizer in accordance with a fifth embodiment of the present invention.

FIG. 15 is a sectional view illustrating the penis erection stabilizer shown in FIG. 14.

FIG. 16 is a sectional view taken along the line E-E' of FIG. 15.

FIG. 17 is a sectional view illustrating the use of the penis erection stabilizer shown in FIG. 14.

FIG. 18 is a sectional view illustrating a penis erection stabilizer in accordance with a sixth embodiment of the present invention.

DESCRIPTION OF REFERENCE NUMERALS FOR MAIN PARTS IN DRAWINGS

10: penis 100: penis erection stabilizer
110: stabilizer body 111: seating groove
112: through-hole 114: small diameter portion
120: stimulus protrusions
122: prominences and depressions
130: cylindrical member 134: magnet

BEST MODE FOR CARRYING OUT THE INVENTION

Reference will now be made in greater detail to preferred embodiments of the invention, examples of which are illustrated in the accompanying drawings.

FIGS. 1 through 4 are views illustrating a penis erection stabilizer in accordance with a first embodiment of the present invention, FIGS. 5 through 7 are views illustrating a penis erection stabilizer in accordance with a second embodiment of the present invention, FIG. 8 is a view illustrating a penis erection stabilizer in accordance with a third embodiment of the present invention, FIGS. 9 through 13 are views illustrating a penis erection stabilizer in accordance with a fourth embodiment of the present invention, FIGS. 14 through 17 are views illustrating a penis erection stabilizer in accordance with a fifth embodiment of the present invention, and FIG. 18 is a view illustrating a penis erection stabilizer in accordance with a sixth embodiment of the present invention.

First, referring to FIGS. 1 through 4, a penis erection stabilizer 100 in accordance with a first embodiment of the present invention includes a cylindrical stabilizer body 110 which is mounted on the outer surface of the penis 10 and has a through-hole 112 defined through the center portion thereof.

In detail, the penis erection stabilizer 100 according to the present embodiment has a cylindrical configuration and includes the stabilizer body 110 in which the through-hole 112 is defined through the center portion thereof so that the penis 10 can be inserted through the through-hole 112, wherein the stabilizer body 110 has a length of 20~25 mm and the through-hole 112 has a diameter of 25~30 mm.

The diameter and the length of the through-hole 112 may be changed to have various sizes, and the stabilizer body 110 can be formed of various materials such as synthetic resin, metal or jade which is harmless to the human body.

When the stabilizer body 110 is injection-molded using synthetic resin, it is preferred that nanosilver be added or pure silver be coated on the outer surface of the stabilizer body 110 so that the antibiosis of the penis erection stabilizer can be elevated.

The small diameter portion 114 is formed at the front end of the through-hole 112 such that the small diameter portion 114 has a diameter less than that of the through-hole 112. It is preferred that the small diameter portion 114 have a diameter of 23~27 mm and be formed to have various sizes.

In this way, since the small diameter portion 114 is formed to inwardly project into the through-hole 112, when the penis erection stabilizer 100 according to the present embodiment is put on the penis 10, as the blood flows into the penis 10 through an artery, the blood is gradually supplied to the spongy tissue of the penis 10 through the through-hole 112 having a relatively large diameter and then the small diameter portion 114 to expand the penis 10 so that the erection of the penis 10 can be improved. When the blood is discharged through the vein of the penis 10 after being supplied to the penis 10, because the blood first passes through the small diameter portion 114 having the abruptly decreasing diameter compared to the penis 10, the discharge of the blood is impeded so that the duration of the erected state of the penis 10 can be extended.

Due to the fact that the small diameter portion 114 is formed at the front end of the through-hole 112 in the stabilizer body 110, when compared to the conventional penis erection stabilizer composed of several parts, the manufacture of the penis erection stabilizer 100 according to the present embodiment can be simplified, and the probability of being disposed due to the loss of a part can be eliminated.

A urethra groove 116 is defined in the through-hole 112 of the stabilizer body 110 and extends in an axial direction to prevent the urethra from being clogged when putting on the penis erection stabilizer 100 according to the present embodiment.

Also, stimulus protrusions 120 are formed on the outer surface of the stabilizer body 110 to promote a female's stimulus when having the sexual act. Of course, the stimulus protrusions 120 can also perform an auxiliary function of preventing the penis erection stabilizer from slipping while putting on and off the penis erection stabilizer 100.

With the penis erection stabilizer 100 according to the present embodiment, configured as described above, put on the penis 10, when a male ejaculates or loses tension due to fatigue while having the sexual act, the blood supplied to the spongy tissue of the penis 10 is fed back through the vein. In this case, because the blood in the expanded penis 10 should first pass through the small diameter portion 114 having the abruptly decreasing diameter, the small diameter portion 114 performs the function of keeping the blood so that the discharge of the blood is retarded. In this way, the erected state of the penis 10 can be maintained for a time sufficient for the completion of the sexual act.

FIGS. 5 through 7 illustrate a penis erection stabilizer 100 in accordance with a second embodiment of the present invention. Prominences and depressions 122 for preventing slippage are formed at regular intervals on the outer surface of the rear portion of the stabilizer body 110, and a plurality of stimulus protrusions 120 are formed on the outer surface of the front portion of the stabilizer body 110.

Therefore, when mounting and removing the penis erection stabilizer according to the present invention on and from the penis 10, by grasping the prominences and depressions 122 for preventing slippage, slippage can be prevented so that the penis erection stabilizer can be conveniently used.

FIG. 8 illustrates a penis erection stabilizer 100 in accordance with a third embodiment of the present invention. A seating groove 111 is defined on the outer surface of the stabilizer body 110.

A cylindrical member 130 made of silicon is fitted into the seating groove 111. A plurality of stimulus protrusions 132 are formed on the outer surface of the cylindrical member 130 made of silicon. At this time, the stimulus protrusions 132 are formed on the cylindrical member 130 made of silicon in such a way as to project forward on the stabilizer body 110 so that stimulus rendered by stimulus protrusions 132 having a predetermined degree of elasticity can be maximized.

By the above-described configuration, after the penis erection stabilizer 100 according to the present embodiment is used, the cylindrical member 130 made of silicon is decoupled from the seating groove 111 of the stabilizer body 110 to be reused after being cleaned.

FIGS. 9 through 13 illustrate a penis erection stabilizer 100 in accordance with a fourth embodiment of the present invention. A plurality of anti-slippage prominences and depressions 122 and stimulus protrusions 120 are formed on the outer surface of the stabilizer body 110. A plurality of magnets 134 having magnetic force no less than 400 Gausses are installed at regular intervals on the inner surface of the stabilizer body 110 in the through-hole 112 so that smooth blood circulation can be ensured and the metabolism of the human body can be promoted to increase health.

While it is illustrated that two magnets 134 are installed in the front portion of the through-hole 112 and three magnets 134 are installed in the rear portion of the through-hole 112, it is to be readily understood that an increased or decreased number of magnets can be installed on the inner surface of the stabilizer body 110 as the occasion demands.

FIGS. 14 through 17 illustrate a penis erection stabilizer 100 in accordance with a fifth embodiment of the present invention. A plurality of anti-slippage prominences and depressions 122 are formed on the outer surface of the rear portion of the stabilizer body 110, and a seating groove 111 is formed on the outer surface of the front portion of the stabilizer body 110.

A cylindrical member 130 made of silicon is fitted into the seating groove 111. A plurality of stimulus protrusions 132 are formed on the outer surface of the cylindrical member 130 made of silicon to project forward on the stabilizer body 110. Meanwhile, a plurality of magnets 134 are installed in the through-hole 112.

FIG. 18 illustrates a penis erection stabilizer 100 in accordance with a sixth embodiment of the present invention. The through-hole 112 of the stabilizer body 110 has a diameter that gradually decreases in a forward direction and forms a taper 112a, and the small diameter portion 114 is formed at the front end of the taper 112a.

By this configuration, the blood can be smoothly supplied to the penis 10 and then stay in the spongy tissue of the penis 10 so that the duration of the erected state of the penis 10 can be further extended.

Although preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A penis erection stabilizer wherein a through-hole (112) is defined through a center portion of a stabilizer body (110) having a cylindrical configuration so that the penis (10) can be inserted through the through-hole (112), and a small diameter portion (114) having a diameter less than that of the through-hole (112) is formed at a front end of the through-hole (112), wherein a seating groove (111) is defined on an outer surface of the stabilizer body (110), and a cylindrical member (130) having a plurality of stimulus protrusions (132) formed on an outer surface thereof is fitted into the seating groove (111).

2. The penis erection stabilizer according to claim 1, wherein a urethra groove (116) is additionally defined in the through-hole (112) to extend in an axial direction.

3. The penis erection stabilizer according to claim 1, wherein a plurality of stimulus protrusions (120) are formed on an outer surface of the stabilizer body (110) to project outward.

4. The penis erection stabilizer according to claim 1, wherein anti-slippage prominences and depressions (112) are formed at regular intervals on an outer surface of a rear portion of the stabilizer body (110), and a plurality of stimulus protrusions (120) are formed on an outer surface of a front portion of the stabilizer body (110).

5. The penis erection stabilizer according to claim 1, wherein the cylindrical member (130) is made of silicon.

6. The penis erection stabilizer according to claim 1, wherein at least one magnet (134) is installed in the through-hole (112).

7. The penis erection stabilizer according to claim 1, wherein the through-hole (112) of the stabilizer body (110) has a tapered surface (112a), and a small diameter portion (114) is formed at a front end of the tapered surface (112a).

* * * * *